US006955923B2

(12) United States Patent
Hartting

(10) Patent No.: US 6,955,923 B2
(45) Date of Patent: Oct. 18, 2005

(54) DEVICE AND METHOD FOR INVESTIGATING THE FLOWABILITY OF A PHYSIOLOGICAL FLUID SAMPLE

(75) Inventor: Herbert Hartting, Altrip (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 389 days.

(21) Appl. No.: 10/226,958

(22) Filed: Aug. 23, 2002

(65) Prior Publication Data

US 2003/0064505 A1    Apr. 3, 2003

(30) Foreign Application Priority Data

Aug. 24, 2001 (DE) ................................ 101 40 699

(51) Int. Cl.⁷ .......................... G01N 1/10; G01N 33/86
(52) U.S. Cl. ..................... 436/180; 436/63; 436/69; 436/52; 436/164; 422/58; 422/68.1; 422/73; 422/81; 422/82.05; 422/82.09; 435/287.1; 600/369; 73/64.41; 73/64.43
(58) Field of Search .................... 436/63, 69, 52, 436/164, 165, 180; 422/58, 68.1, 73, 81, 422/82.05, 82.09; 435/2, 13, 287.1; 600/369; 73/64.41, 64.43

(56) References Cited

U.S. PATENT DOCUMENTS

| | | | | |
|---|---|---|---|---|
| 3,486,859 A | * | 12/1969 | Greiner et al. ................ | 436/69 |
| 3,911,728 A | * | 10/1975 | Fixot .......................... | 73/54.04 |
| 4,756,884 A | * | 7/1988 | Hillman et al. ............... | 422/73 |
| 4,780,418 A | * | 10/1988 | Kratzer ........................ | 436/69 |
| 4,849,340 A | | 7/1989 | Oberhardt .................... | 435/13 |
| 5,039,617 A | * | 8/1991 | McDonald et al. ........... | 436/69 |
| 5,110,727 A | | 5/1992 | Oberhardt .................... | 435/13 |
| 5,302,348 A | * | 4/1994 | Cusack et al. ................ | 422/73 |
| 5,350,676 A | | 9/1994 | Oberhardt et al. ............ | 435/13 |
| 5,591,403 A | | 1/1997 | Gavin et al. .................. | 422/73 |
| 5,628,961 A | * | 5/1997 | Davis et al. .................. | 422/63 |
| 5,658,723 A | | 8/1997 | Oberhardt .................... | 435/4 |

FOREIGN PATENT DOCUMENTS

| | | | | |
|---|---|---|---|---|
| DE | 2406484 | | 1/1975 | .......... G01N 11/04 |
| DE | 3541057 A1 | | 5/1987 | .......... G01N 33/86 |
| DE | 3853457 T2 | | 5/1995 | ............ G01N 1/12 |

OTHER PUBLICATIONS

Lambert. J., "Eine neue Versuchsanordnung für die direkte mikroskopische Beobachtung des FlieBverhaltens von Blut in Modellen natürlicher und künstlicher GefäBsystems—A new experimental set-up for the direct microscopic observation of the flow behaviour of blood in models of natural and artifical vessel systems." Biomedizinische Technik. vol. 20. (1975) pp. 139-143.

* cited by examiner

Primary Examiner—Maureen M. Wallenhorst

(57) ABSTRACT

To investigate the flowability of a physiological fluid sample, an uptake passage (12) for the fluid sample (16), an actuator device (18) for the cyclic change in orientation of measuring particles (14) in the fluid sample (16), and a detector device (20, 22) for the preferably optical detection of the change in orientation of the measuring particles (14) are provided. In order to make reliable measurements possible with minimal instrument expense, it is proposed that the actuator device is formed by a pump unit (18) to produce a flow of the fluid sample (16) that travels back and forth along the uptake passage (12) and indicates the change in orientation of the measuring particles (14).

24 Claims, 3 Drawing Sheets

DEVICE AND METHOD FOR INVESTIGATING THE FLOWABILITY OF A PHYSIOLOGICAL FLUID SAMPLE

The invention concerns a device and a method for investigating the flowability of a physiological fluid sample, in particular a blood sample for coagulation tests, according to the preamble of claims 1 and 21, respectively.

A coagulation test system of this type was made known in U.S. Pat. No. 5,110,727. With this system, blood coagulation or coagulation-dissolution tests are to be made possible ex vivo using simple means, e.g., to monitor the effect of anti-coagulants. Iron oxide particles are used as measuring particles in this system, which said iron oxide particles are dispersed in the sample in a measuring capillary and are subjected to an oscillating magnetic field. As a result, the measuring particles move in step with the magnetic field changes and change accordingly in terms of transparency or reflectivity in the measuring range of a detector unit. As sample clotting increases, the particle movement is inhibited, and the measuring signal remains constant. A magnet system comprising a bias-voltage permanent magnet and an electromagnet operated using alternating current are used as actuator. In order to ensure that the necessary flux density changes are achieved, relatively large coils and high currents must be used, which is disadvantageous in terms of weight and power supply, especially in the case of a portable device.

Based on this, the invention is based on the object of preventing the disadvantages of the related art, and improving a measuring system of the type described initially so that reliable and reproducible test results are obtained with simple handling and minimal instrument expense.

The combination of features indicated in claim 1 and claim 21 is proposed in order to attain this object. Advantageous embodiments and further developments of the invention result from the dependent claims.

With regard for a measuring system, it is proposed according to the invention, that the actuator device is formed by means of a pump unit for producing a flow of the fluid sample that represents the change in orientation of the measuring particles and travels back and forth along the uptake passage. This makes it possible to use non-magnetic measuring particles, which can be optimized further in terms of the detection method. In contrast to a magnetic alternating field, an oscillating flow can be produced with low energy consumption and simple constructive means. The system according to the invention does not require expensive manipulation, and makes an automatic measuring sequence possible using the smallest quantities of sample. Since the movement of the measuring particles is induced by means of an alternating flow, production tolerances and the internal surface properties of the sample uptake passage play a subordinate role, and susceptibility to air bubble inclusions is minimized.

According to a preferred embodiment, it is provided that the pump unit comprises an, in particular, mechanically, pneumatically or piezoelectrically actuated displacer to act on the fluid sample in the uptake passage using suction and pressure in a cyclically alternating fashion. A further design simplification can be achieved in that the pump unit comprises a flexible displacement membrane that partially borders the uptake passage. To produce flow effectively, the pump unit should be connected to a pump site in the region of a closed or closeable end portion of the uptake passage.

In terms of production engineering, it is advantageous for larger piece numbers in particular when the uptake passage is formed by a recess in an intermediate layer of a multi-layered plastic sheet film interconnection body.

A further advantageous embodiment of the invention provides that the uptake passage is designed—at least in sections—as a capillary passage. This makes it possible to investigate the smallest sample quantities, and the sample fluid can be taken up in a self-suctioning fashion. In addition, high flow gradients and, therefore, an effective orientation of the measuring particles is achieved via a capillary cross-section.

A further improvement is achieved in that the measuring particles are non-spherical, long-straggling and/or flattened in shape. As a result, the particles become oriented transverse to the direction of flow in the shear field of the sample flow, so that, ultimately, a high detection sensitivity can be achieved. It is hereby favorable if the ratio of the longitudinal dimension to the transverse dimension of the measuring particle is greater than 2, preferably greater than 10. The measuring particles are preferably designed as pigments, preferably as platelet-shaped effect pigments, or as rod-shaped or fiber-shaped formations, in particular as whiskers.

In order to reduce disturbing influences on the sample, it is advantageous when the measuring particles are enclosed in a polymeric or oligomeric protective layer.

In fluid samples without solid particles, the measuring particles are suspended as a foreign substance, although it is also feasible that the measuring particles are formed by sample components, in particular erythrocytes in a whole blood sample.

In a preferred embodiment, the detector device comprises a radiation source and a radiation receiver for electromagnetic radiation, preferably a light diode and an optoelectronic semiconductor sensor. The detection is advantageously based on the fact that the measuring particles absorb and/or reflect incident electromagnetic radiation differently depending on the angle of incidence. For direct detection, the walls of the uptake passage should be permeable to the measuring radiation of the detector device, at least in sections.

In order to create reproducible measuring conditions, it is advantageous if the uptake passage is coupled to a tempering device for adjusting a specified temperature of the fluid sample.

An evaluation unit is provided for the automatic determination of a test parameter according to the change in orientation of the measuring particles detected as a function of time.

To perform coagulation tests, the following are proposed in particular: a measuring device having a capillary passage to take up a blood sample containing measuring particles or to which measuring particles have been added, a pump unit for producing a flow of the blood sample that varies the orientation of the measuring particles and travels back and forth along the uptake passage, and a detector device for the preferably optical detection of the change in orientation of the measuring particles.

In terms of the method, the object described hereinabove is attained in that a flow of the fluid sample traveling back and forth in the uptake passage is produced for the cyclically changeable orientation of the measuring particles. The fluid sample is subjected to a shear flow in the uptake passage, so that the measuring particles are oriented in synchroneity depending on the direction of flow.

In a preferred embodiment, the change in orientation of the measuring particles is detected as an alternating change in the reflectance or absorption capability of the fluid sample using an optical detector device.

To perform coagulation tests, the change in orientation of measuring particles is recorded via a plurality of cycles, and is evaluated as a function of time to determine a variable, in particular the prothrombin time (PT), the activated clotting time (ACT) or the activated partial thromboplastin time (aPTT).

The invention will be described in greater detail hereinbelow with reference to schematic drawings in exemplary embodiments.

Figure 1:
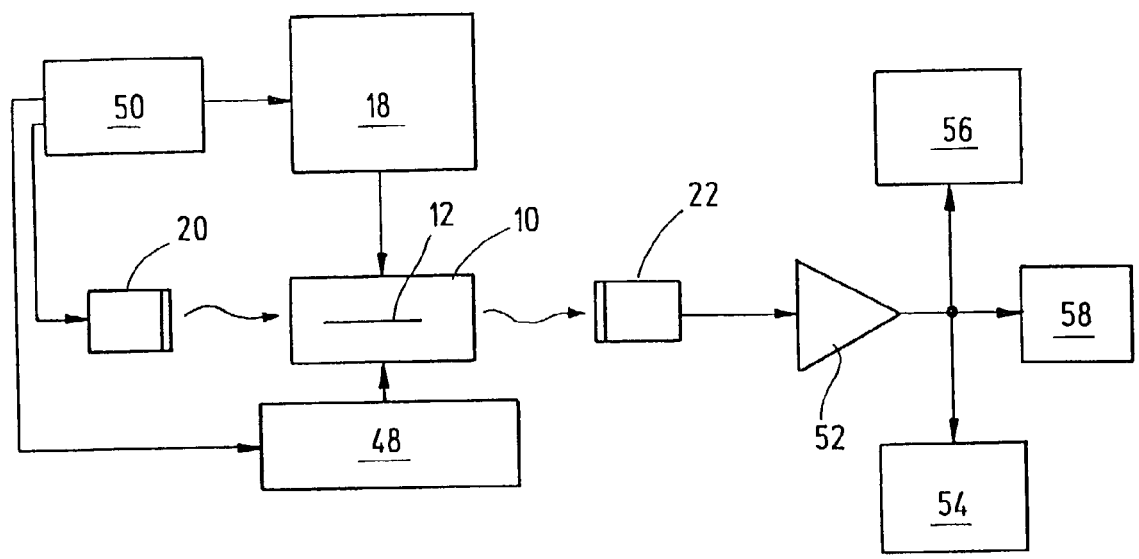
FIG. 1 is a view of a block diagram of a device or a measuring system for performing coagulation tests on blood samples.

The measuring device shown in the drawing for performing coagulation tests on blood samples basically comprises a sample carrier 10 having an uptake passage 12 for a blood sample 16 to which measuring particles 14 have been added, a pump unit 18 for producing a back and forth flow of the blood sample in the uptake passage, and a detector device 20, 22 for the optical detection of the flow-induced change in orientation of measuring particles 14 as an indirect measure of viscosity.

Figure 3:
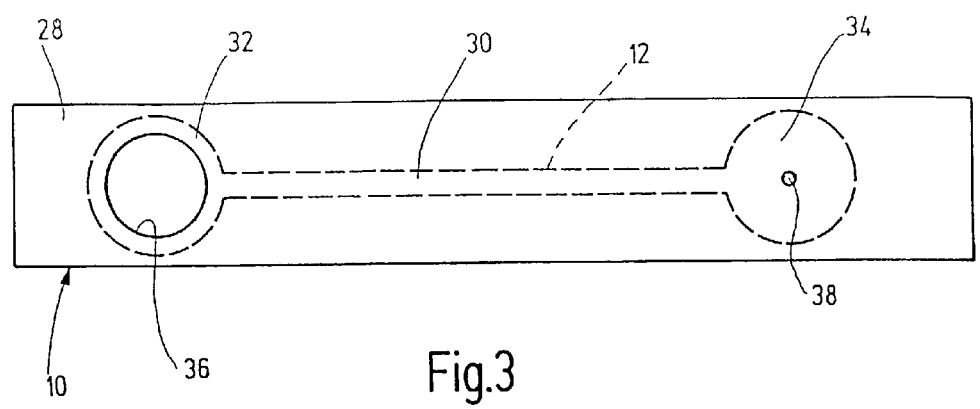
FIGS. 3 and 4 are views of a sample carrier of the measuring system with an uptake passage for a blood sample in top view and vertical cut.
Figure 4:
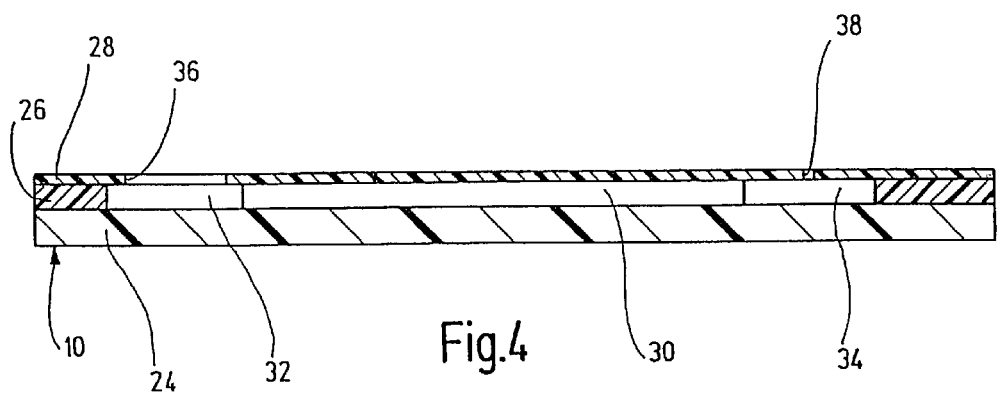

The sample carrier 10 shown in FIGS. 3 and 4 comprises a multi-layered plastic interconnection body, a rigid base plastic sheet film 24, an intermediate plastic sheet film 26 and a flexible, transparent cover plastic sheet film 28. A recess forming the uptake passage 12 is stamped in the intermediate plastic sheet film, which said recess comprises a capillary-shaped passage section 30 and a sample uptake chamber 30 attached thereto on the opening side, and a pump chamber 34. The sample uptake chamber 32 can be filled via an intake opening 36 in the cover plastic sheet film 28, while the pump chamber 34 communicates with the atmosphere via a vent opening 38 in the cover plastic sheet film 28.

Figure 2:
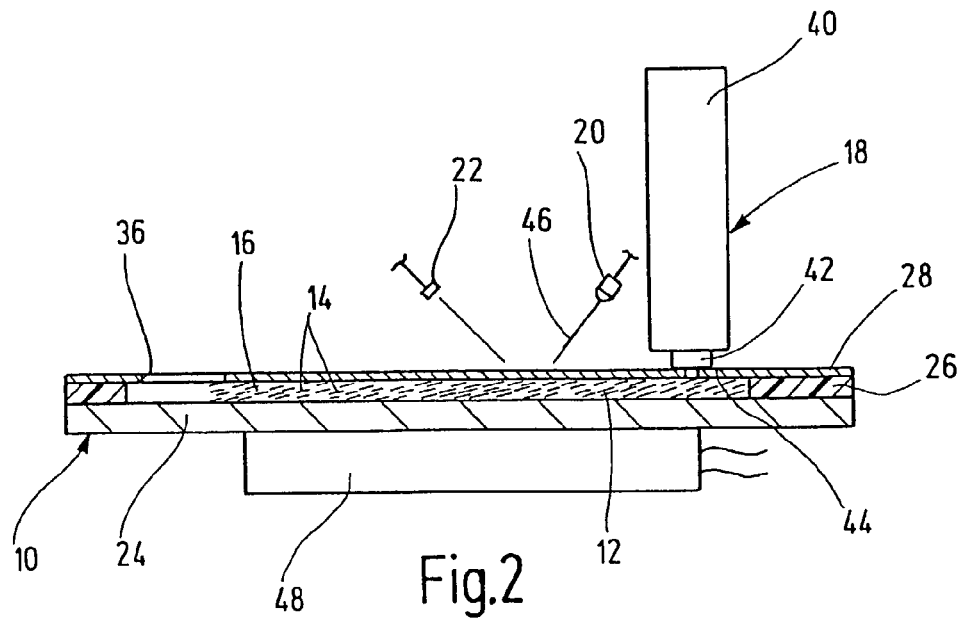
FIG. 2 is a view showing the measuring system in illustrative fashion.

As shown in FIG. 2, the pump unit 18 can comprise a stamp 42 driven by means of a piston drive 40, which said stamp can be placed on the cover plastic sheet film 28 over the pump chamber 34 and close the vent opening 38. The flexible cover plastic sheet film 28 thereby functions as displacer 44 for acting on the blood sample in the uptake passage 12 with suction and pressure in a cyclically alternating fashion. It is understood that other, in particular, pneumatically or piezoelectrically-operating actuation means can be used to produce a back and forth-moving fluid stream.

The detector device includes a light diode 20 as radiation source that radiates through the cover plastic sheet film 28 into the capillary portion 30 of the uptake passage 12, as well as a photosensor 22 oriented accordingly to detect the measurement radiation 46 reflected by the blood sample or radiated through said blood sample.

As described hereinbelow in greater detail, the measuring principle is based on the fact that the orientation of measuring particles located in the blood sample changes depending on the sample viscosity by means of the pressure change acting on the blood sample, which can be detected via the change in optical properties in the beam path of the detector device 20, 22. As long as the blood sample is in motion, the optical properties fluctuate. If coagulation occurs, they remain constant.

In order to bring the fluid sample to a defined measuring temperature, a heating device 48 is provided that is in thermally-conductive contact with the uptake passage 12 via the base plastic sheet film 24. The control of the measuring sequence takes place via a control device 50 connected to the units 18, 20, 48 on the output side.

For the further processing and evaluation of the measuring signals of the photosensor 22, a measuring amplifier 52, a signal recorder 54, an evaluation unit 56 with real-time clock, and a display unit 58 are provided. The evaluation unit 56 includes an A/D converter installed after the measuring amplifier 52 for the time-dependent digitization of the measuring signal, and a digital processing unit designed as a microcontroller for determining test parameters from the signal behavior. The entire measuring device can be placed in a portable-battery-operated manual device, so that the intended tests can be carried out regardless of location.

Figure 5:
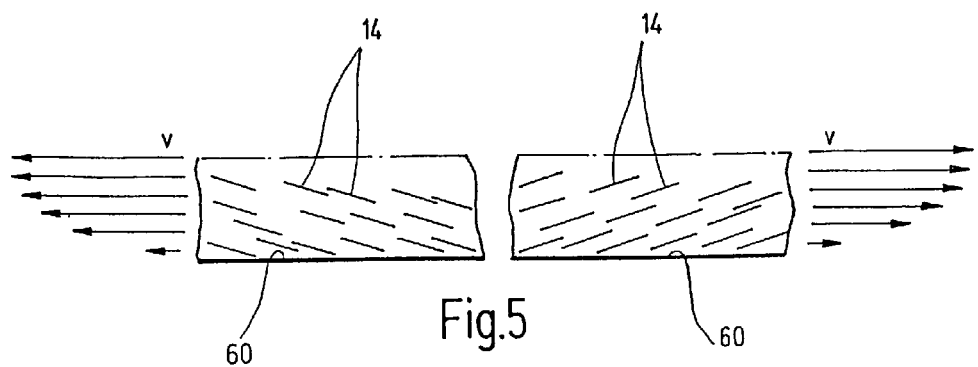
FIG. 5 is a sectional view of the uptake passage with measuring particles located therein in the case of back and forth flow.

As shown in FIG. 5, the measuring particles 14 are subjected to a shear flow in the capillary portion 30 of the uptake passage 12, as illustrated using the flow arrows for the two directions of flow shown. The flow rate v is therefore greatest in the middle of the passage, and it diminishes toward the passage wall 60 in the case of laminar flow in the form of a parabola. In the case of given anisotropic particle geometry, this leads to a transverse orientation of the measuring particles 14 that is identical for all said measuring particles, with their longitudinal axes transverse or diagonal to the direction of flow at that instant, whereby a corresponding change in orientation takes place based on the periodic reversal of flow.

Platelet-shaped pigments and special effect pigments are preferably provided as suitable anisotropic measuring particles. The property of these pigments to reflect or absorb the incident electromagnetic radiation depending on the angle is significant for the detection, so that pronounced changes in brightness are retained depending on the respective orientation angle.

Interference effect pigments are composed of a flat mica plate as the carrier, which said mica plate is coated with a heavily-refracting metal oxide such as titanium dioxide. If the coating is thin, silver-white colors occur. As the thickness of the coating increases, however, yellow, red, blue and, finally, green pearly lustre pigments are obtained. Such pigments are supplied by various manufacturers, such as Merck, KGaA, Darmstadt, Germany, under the trade name Iriodin.

In order to rule out effects on the coagulation behavior, the surface of the pigments used can be modified using polymeric or oligomeric protective layers. Suitable protective layers of this type include uncharged, synthetic polymers (such as polyethylene, polypropylene, polysilicone, polytetrafluoroethylene, and polystyrene), hydrophilic, uncharged polymers (such as polyethylene glycol, polyvinyl pyrrolidone), or positively-charged polymers, such as heparin derivatives. These polymers or oligomers of them can be fixed on the pigment surface in different fashions, in particular by means of chemical bonding or simple coating, as is the case in terms of coating with polystyrene from solution). Layers based on polyethyleneglycol or polyvinyl pyrrolidone are particularly preferred.

To perform a coagulation test, the uptake passage 12 is coated on its internal surface with a reagent mixture containing thromboplastins as well as the measuring particles 14. A sufficient aliquot of a blood sample, e.g., 50 μl are applied to the sample application chamber 32 using a transfer instrument, and suctioned into the uptake passage 12 automatically by means of capillary effect. Any air that is present escapes through the vent opening 38. The reagent mixture is taken up in the inflowing blood, and the measuring particles (e.g., 0.2 mg effect pigments) are thereby distributed. In order to ensure a defined sequence of the complex enzymatic reactions, a constant temperature of 39° C., for example, is maintained by means of a heating device 48.

Figure 6:
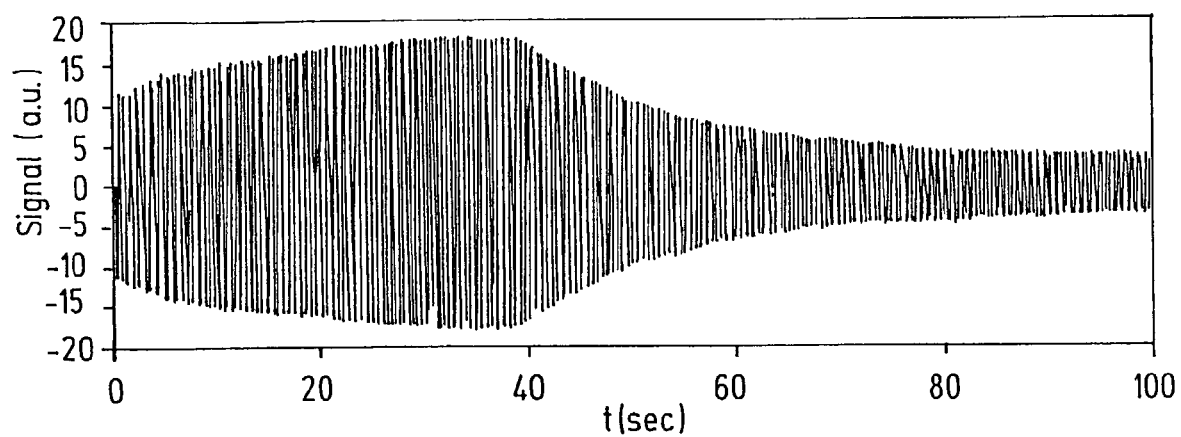
FIG. 6 is a time diagram of a measuring signal reflecting the change in orientation of measuring particles.
Figure 7:
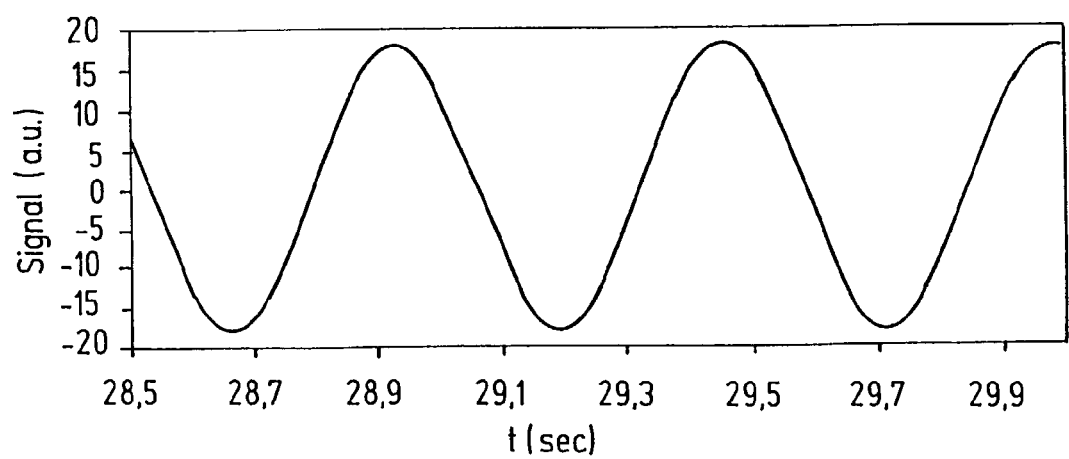
FIG. 7 shows a slow-motion section of the signal behavior according to FIG. 6.

To produce the alternating flow, a low-frequency pressure and suction-producing change of stroke is carried out on the blood sample in the passage 12 using the pump unit 18 in the range of a few Hertz. Due to the flow-induced movement of the measuring particles 14, the brightness changes in the detection range of the detector device 20, 22 with the same frequency. Accordingly, an oscillating AC signal is available at the output of the amplifier 52, as shown in FIGS. 6 and 7 in random units over time. During one initial increase interval, the measuring particles 14 move back and forth in stacked formation in the shear field of the flow increasingly in synchroneity. As soon as coagulation occurs, the motion is inhibited and the signal amplitude drops off accordingly.

Based on the signal drop, a test parameter for the blood coagulation reaction, such as prothrombin time, can be determined using a suitable algorithm in the evaluation unit 56 with consideration for specific influencing variables and scaling factors.

It is understood that, according to the principle described hereinabove, the flow behavior or viscosity changes can be investigated not only in blood samples, but in any fluid samples and, in particular, in other physiological fluids such as plasma, saliva, tissue fluid, milk, etc. To modify properties of the medium, additives such as moistening agents and preservatives, activators and buffers can be added. It is possible, in principle, that the sample itself delivers measurable components, e.g., in that erythrocytes are used as disk-shaped measuring particles in a blood sample. Instead of using a geometrical optical detection of particle movement, it is also feasible to use other contactless, e.g., capacitively-functioning detection methods.

What is claimed is:

1. A device for investigating the flowability of a physiological fluid sample comprising an uptake passage for the fluid sample, an actuator device for providing cyclic change in orientation of measuring particles in the fluid sample, and a detector device for detecting the change in orientation of the measuring particles, and wherein the actuator device is formed by a pump unit that produces a flow of the fluid sample that travels back and forth along the uptake passage and effects the change in orientation of the measuring particles.

2. The device according to claim 1, wherein, the pump unit comprises a mechanically, pneumatically, or piezoelectrically actuated displacer for acting upon the fluid sample in the uptake passage to provide suction and pressure in a cyclically changing fashion.

3. The device according to claim 1, wherein, the pump unit comprises a flexible displacement membrane that partially borders the uptake passage.

4. The device according to claim 1, wherein, the pump unit is connected to a pump site positioned in a region of a closed or closeable end portion of the uptake passage.

5. The device according to claim 1, wherein the uptake passage is formed by a recess in an intermediate layer of a multi-layer plastic sheet film interconnecting body.

6. The device according to claim 1, wherein at least a portion of the uptake passage is designed as a capillary passage.

7. The device according to claim 1, wherein the measuring particles are non-spherical, long-straggling and/or flattened in shape.

8. The device according to claim 1, wherein a ratio of a longitudinal dimension to a transverse dimension of the measuring particles is greater than 2.

9. The device according to claim 1, wherein the measuring particles are platelet-shaped pigments.

10. The device according to claim 1, wherein the measuring particles are rod-shaped or fiber-shaped formations.

11. The device according to claim 1, wherein the measuring particles are covered with a polymeric or oligomeric protective layer.

12. The device according to claim 1, wherein the measuring particles are suspended in the fluid sample as a foreign substance.

13. The device according to claim 1, wherein the fluid sample is blood and the measuring particles are formed by erythrocytes.

14. The device according to claim 1, wherein the detector device includes a radiation source and a radiation receiver for electromagnetic radiation.

15. The device according to claim 1, wherein the detector device includes a light diode and an opto-electronic semiconductor sensor.

16. The device according to claim 1, wherein the measuring particles absorb and/or reflect incident electromagnetic radiation differently depending on the angle of incidence of electromagnetic radiation.

17. The device according to claim 1, wherein at least a portion of a wall of the uptake passage is permeable to electromagnetic radiation.

18. The device according to claim 1, wherein the uptake passage is coupled to a tempering device for adjusting the temperature of the fluid sample.

19. The device according to claim 1, further comprising an evaluation unit for determining a test parameter according to the change in an orientation detected as a function of time.

20. A device for performing coagulation tests comprising a capillary passage for taking up a blood sample, where the blood sample contains measuring particles, a pump unit for producing a flow of the blood sample that varies the orientation of the measuring particles in cyclic fashion and travels back and forth along the capillary passage, add an optical detector where the change in orientation of the measuring particles is optically detected by said optical detector.

21. A method for investigating the flowability of a physiological fluid sample, comprising the steps of:
    bringing a fluid sample into an uptake passage,
    distributing measuring particles in the fluid sample,
    providing a flow of the fluid sample that travels back and forth in the uptake passage to change the orientation of the measuring particles in cyclic fashion,
    detecting the change in orientation of the measuring particles and determining the flowability of the fluid sample based upon the change in orientation of the measuring particles.

22. The method according to claim 21, wherein the fluid sample is subjected to a shear flow in the uptake passage, so that the measuring particles are oriented differently depending on the direction of flow.

23. The method according to claim 21, wherein the change in orientation of the measuring particles is detected as an alternating change in a reflectance or absorption capability of the fluid sample by means of an optical detector device.

24. The method according to claim 21, wherein the change in orientation of the measuring particles is recorded over a plurality of cycles, and is evaluated as a function of time to determine a prothrombin time (PT), an activated clotting time (ACT) or an activated partial thromboplastin time (aPTT).

* * * * *

UNITED STATES PATENT AND TRADEMARK OFFICE
CERTIFICATE OF CORRECTION

PATENT NO. : 6,955,923 B2
DATED : October 18, 2005
INVENTOR(S) : Harttig

It is certified that error appears in the above-identified patent and that said Letters Patent is hereby corrected as shown below:

Title page,
Item [75], Inventor, should be -- Harttig --.

Signed and Sealed this

Twentieth Day of December, 2005

JON W. DUDAS
*Director of the United States Patent and Trademark Office*